Aug. 23, 1932. C. N. WHITE Plant Pat. 22
ROSE
Filed Jan. 18, 1932
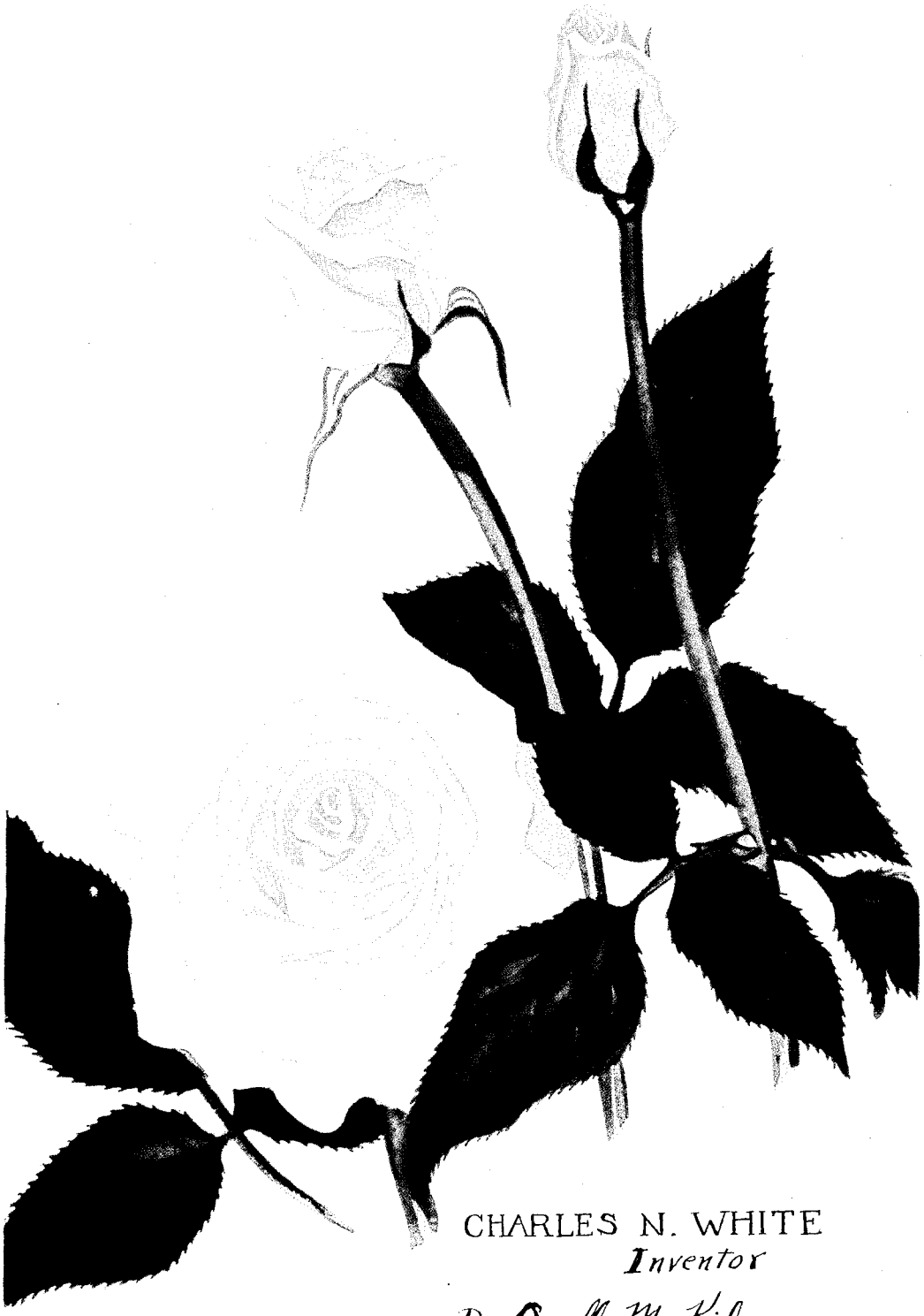
CHARLES N. WHITE
*Inventor*
By *Orville M. Kile*
*Plant Patent Agent*

Patented Aug. 23, 1932

UNITED STATES PATENT OFFICE

CHARLES N. WHITE, OF MEDINA, NEW YORK

ROSE

Application filed January 18, 1932. Serial No. 587,329.

My invention relates to improvements in yellow, semi-double, fragrant hybrid tea roses. The object of my invention is to provide a rose of this type having a distinctive color combined with good form, good blooming and keeping qualities and other desirable characters.

This new variety was first discovered by me on or about April 15, 1929. It originated as a sport of the well-known variety Joanna Hill, which it closely resembles in size and shape of flowers but from which it differs in color of flowers and certain other characters. This variety has been thoroughly tested by me and reproduces asexually true to type and character. My new variety was registered with the American Rose Society in 1931.

The accompanying illustration shows in full color a bud, a half opened flower and a fully opened flower, together with stems and foliage.

The following is a detailed description of my new rose:

A bush or upright rose of free and vigorous growing habits.

Stems, of good length, stoutish, "light bice green" in color according to Ridgeway's Color Standard and Nomenclature (Plate XVII, edition of 1912), no thorns or spines occur above the third or fourth leaf branch counting downward from the flower, and no spines and but few thorns below that point. Such thorns as occur are rather heavy, pinkish in color and curving downward.

Hips rather large and only moderately tapered.

Leaves on flower-bearing stems are medium in size rather than large, not glossy, and "forest green" in color, according to Ridgeway's Color Standard and Nomenclature (Plate XVII).

The edges of the leaves have the appearance under a magnifying glass of being beset with sharp though flexible points, rather than being merely notched or serrated as in most varieties of roses. Each mature leaf-branch bears from 1 to 3 small thorns on its petiole or central stem.

Stipules are medium sized with sharp straight points parallel to the petiole rather than curled or spreading.

Sepals, five in number, rather small—¾ to 1¼ inches long—regular in size, regularly tapered and not foliaceous.

Flowers, medium size, 4 to 4½ inches across when fully opened, semi-double having 23 to 25 large petals in the month of November. In shape the flower is very similar to that of Joanna Hill. The outer whorls of petals have quite a tendency to curl. When fully opened, cut and exposed in ordinary heated room, most of the petals curl back so as to expose only about one-half their area. The outer petals usually curl when the cut flower is half opened thus giving a pointed center effect.

The general color effect is "amber yellow" to "wax yellow." The outer edges of the outer petals are "barium yellow" (all color names refer to Ridgeway's Color Standard and Nomenclature, Plate XVI). The base of each petal is of a deeper shade of yellow than the rest of the petal but both sides of the base are of approximately the same shade. There is no tendency toward the cadmium or copper shades found in Joanna Hill.

The most important character which distinguishes my new rose from the well known variety Joanna Hill, is the color as set forth in detail above. The most important characters which, taken singly or in combination, distinguish my new rose from other yellow, fragrant, hybrid tea roses, aside from differences in shades of color, are:

First, its semi-double character, comprising 23 to 25 large petals;

Second, its tapering, regular, non-foliaceous sepals of medium length;

Third, its vigorous growing habits, with strong stems of "light bice green" color relative free of thorns.

Fourth, its medium sized "forest green" leaves having one to three small thorns on the petioles and midribs and having edges beset with sharp though flexible points, as more particularly described above.

Fifth, its stipules having straight sharp points.

I claim:

The variety of fragrant, semi-double, hybrid tea rose herein shown and described, characterized particularly by its amber yellow color, its vigorous growing habits and relative freedom from thorns.

CHARLES N. WHITE.